United States Patent [19]

Gittos et al.

[11] 3,998,965
[45] Dec. 21, 1976

[54] 4-AMINOALKYL-4-CYANO-4-PHENYL-BUTANOIC ACID ESTERS

[75] Inventors: Maurice Ward Gittos, Slough; David Anthony Amey, Luton, both of England

[73] Assignee: Aspro Nicholas Limited, England

[22] Filed: Dec. 11, 1974

[21] Appl. No.: 531,556

Related U.S. Application Data

[63] Continuation-in-part of Ser. No. 425,876, Dec. 18, 1973, Pat. No. 3,963,729.

[30] Foreign Application Priority Data

Dec. 15, 1973 United Kingdom ............ 58202/73

[52] U.S. Cl. .......................... 424/304; 424/248.54; 424/248.55; 424/248.5; 260/239 B; 260/247.1 R; 260/247.2 A; 260/247.2 B; 260/268 CN; 260/290 H; 260/293.73; 260/293.75; 260/293.78; 260/326.43; 260/465 D; 424/244; 424/250; 424/267; 424/274

[51] Int. Cl.$^2$ .............. A61K 31/275; C07C 121/78
[58] Field of Search ................ 260/465 D; 424/304

[56] References Cited

UNITED STATES PATENTS

| | | | |
|---|---|---|---|
| 3,125,583 | 3/1964 | Leonard | 260/465 X |
| 3,261,859 | 7/1966 | Dengel | 260/465 |

*Primary Examiner*—Lewis Gotts
*Assistant Examiner*—Dolph H. Torrence
*Attorney, Agent, or Firm*—Foster York

[57] ABSTRACT

Alkyl esters, dialkylamides and heterocyclic amides of 4-amino-alkyl-4-cyano-4-phenyl-butanoic and but-2-enoic acids substituted in at least one of the 2 and 3 positions by a $C_1$–$C_4$ alkyl group or by a divalent alkylene radical which together with at least one of the carbon atoms at said 2 and 3 positions forms a carbocyclic ring of 3 to 8 carbon atoms are novel intermediates involved in the preparation of pharmacologically active compounds. They also have pharmacological, in particular central nervous system, especially anti-depressant or cardiovascular activity. Several methods are disclosed for preparing the novel compounds.

4 Claims, No Drawings

4-AMINOALKYL-4-CYANO-4-PHENYL-BUTANOIC ACID ESTERS

This application is a continuation-in-part of our co-pending application Ser. No. 425,876, filed Dec. 18, 1973, now U.S. Pat. No. 3,963,729.

The present invention relates to compounds which are intermediates in the preparation of certain pharmacologically active pyridine derivatives and which have pharmacological, in particular central nervous system or cardiovascular, activity themselves.

We have disclosed in our co-pending U.K. Pat. Application No. 59761/72 certain pyridine derivatives which have pharmacological, in particular central nervous system, especially anti-depressant, activity. These pyridine derivatives are 3-phenyl-3-aminoalkyl-2,6-dioxo-tetra and hexa- hydropyridines substituted in at least one of the 4 and 5 positions of the hydrogenated pyridine ring by a $C_1$–$C_4$ alkyl group or by a divalent alkylene radical which together with at least one of the carbon atoms at said 4 and 5 positions forms a carbocyclic ring of 3 to 8 carbon atoms, and acid addition salts and quaternary ammonium derivatives thereof. The co-pending application discloses also a number of methods of preparing the said pyridine derivatives. Some of those methods involve the intermediate preparation of alkyl esters, dialkylamides and saturated heterocyclic amides of the corresponding 4-aminoalkyl-4-cyano-4-phenyl butanoic and butenoic acids, which compounds are now appreciated as being novel and have also been found to possess pharmacological activity.

According to the present invention therefore, there are provided alkyl esters, dialkylamides and saturated heterocyclic amides of 4-aminoalkyl-4-cyano-4-phenylbutanoic and but-2-enoic acids which are substituted in at least one of the 2 and 3 positions by an alkyl group of 1 to 4 carbon atoms or by a divalent alkylene radical which together with at least one of the carbon atoms at said 2 and 3 positions forms a carbocyclic ring of 3 to 8 carbon atoms and acid addition salts thereof. The phenyl radical in the 4 position may be substituted further by one or more substituents which are "therapeutically compatible" (as hereinafter defined) with the molecule.

The term therapeutically compatible is used in this Specification in relation to a substituent to mean that the presence of that substituent neither destroys the pharmacological activity of the molecule nor so decreases said activity and/or increases the toxicity of the molecule that the therapeutic ratio is reduced to five or below. The therapeutic compatibility of a particular substituent may depend upon the intended site of substitution in the molecule and/or the presence in the molecule of other substituents. Hence a given substituent may be therapeutically compatible in respect of one molecule into which it is introduced but incompatible, i.e. inactivating, in respect of another molecule. The compatibility of any substituent in respect of any compound of the invention can be readily assessed by subjecting the relevant substituted compound to standard screening tests such as those referred to hereinafter. It is well within the ability of the averagely skilled man concerned with the development of new drugs to ascertain which substituents may be present and at what positions in pharmacologically active compounds of the invention.

Examples of substituents in the phenyl ring likely to be therapeutically compatible with all compounds of the invention are $C_1$–$C_4$ alkyl optionally substituted by hydroxy or $C_1$–$C_4$ alkoxy, hydroxy, $C_1$–$C_4$ alkoxy, halogen and trifluoromethyl. It is presently preferred that the phenyl ring should be unsubstituted or substituted by at least one $C_1$–$C_4$ alkoxy, especially methoxy, or halogen, especially chlorine.

The alkyl or alkylene radicals (including moieties) in compounds of the present invention may be straight or branched chain, saturated or unsaturated hydrocarbon radicals. Unless otherwise stated, it is preferred that each hydrocarbon radical is saturated and contains 6, more especially 4, carbon atoms or less. Any reference in this Specification to a specific alkyl or alkylene radical having structural isomers includes all of those isomers and mixtures thereof unless a particular isomer is specified. Examples of alkyl radicals are methyl, ethyl, propyl, butyl, amyl, hexyl, ethenyl, ethynyl, propenyl (especially allyl), propynyl (especially propargyl), butenyl and butynyl. Preferred alkyl radicals are methyl and ethyl and preferred alkylene radicals are 1,2-ethylene and 1,3-propylene for the alkylene moiety of the aminoalkyl group and 1,4-butylene and 1,5-hexylene for $R_1$ and $R_2$ or $R_3$.

The amino moiety of the 4-aminoalkyl substituent may be a primary or, preferably, secondary or tertiary amino group. When said amino moiety is secondary or tertiary, the amino nitrogen atom can be attached to, for example, $C_3$ to $C_6$ cycloalkyl or $C_1$ to $C_4$ alkyl optionally substituted by $C_3$–$C_6$ cycloalkyl or by phenyl, which itself may be substituted by, for example, one or more alkoxy groups. An alkyl group attached to the nitrogen atom may be attached also to the alkylene chain to form with said chain and nitrogen atom a saturated heterocyclic amine alkyl radical, e.g. piperidylalkyl, pyrrolidinyl alkyl, or homopiperidylalkyl. An example of such a heterocyclic amine alkyl radical is 2-(N-methyl-piperidin-2'-yl)ethyl. Alternatively, when the amino group is tertiary, the amino nitrogen atom may be part of a heterocyclic ring, especially a six-membered alkylene-imino in which one or more carbon atoms optionally are replaced by oxygen or nitrogen. Examples of such alkylene-imino groups are piperidino, piperazino and morpholino. Preferably, the amino group is di($C_1$ to $C_4$) alkylamino, especially dimethyl- or diethyl-amino.

A preferred class of compounds of the present invention are those of formula 1.

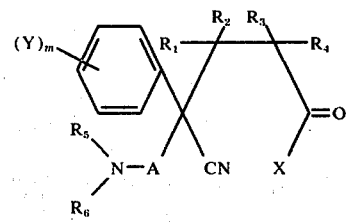

wherein $R_1$, $R_2$ and $R_3$ independently represent hydrogen or $C_1$–$C_4$ alkyl and $R_4$ represents hydrogen, $C_1$–$C_4$ alkyl or $C_2$–$C_5$ alkoxycabonyl, provided that at least one of $R_1$, $R_2$, $R_3$ and $R_4$ represents alkyl, or $R_1$ together with $R_2$ or with $R_3$ represents an alkylene radical which together with their immediately adjacent carbon atom(s) forms a carbocyclic ring of 3 to 8 carbon atoms and $R_3$ or $R_2$ respectively and $R_4$ are as defined above (not subject to the proviso), or $R_2$ and $R_4$ together represent a second valency bond joining their immediately adjacent carbon atoms, or $R_1$ together with $R_3$ represents a second valency bond joining their immediately adjacent carbon atoms and $R_2$ and $R_4$ are as defined above provided that at least one of them represents alkyl;

Y represents $C_1$–$C_4$ alkyl optionally substituted by hydroxy or $C_1$–$C_4$ alkoxy, hydroxy, $C_1$–$C_4$ alkoxy, halogen or trifluoromethyl;

m represents zero or an integer up to 5;

A represents $C_1$–$C_6$ alkylene; and $R_5$ represents $C_1$–$C_4$ alkyl optionally substituted by $C_3$–$C_6$ cycloalkyl, or $C_3$–$C_6$ cycloalkyl and $R_6$ represents hydrogen or $C_1$–$C_4$ alkyl optionally substituted by phenyl, or $R_5$ together with $R_6$ represents an alkylene radical optionally interrupted by oxygen or nitrogen and which together with the amino nitrogen atom constitutes a saturated five or six-membered heterocyclic ring; and X represents D. alkyl or $NR_7R_8$, wherein D represents oxygen or sulphur and $R_7$ and $R_8$ represent the same or different alkyl groups or together represent a saturated alkylene radical optionally substituted by oxygen or nitrogen, which alkylene radical with the adjacent nitrogen atom forms a heterocyclic ring; and acid addition salts thereof.

In the alkyl esters of formula 1, it is preferred that D represents oxygen and that the alkyl group attached thereto contains from 1 to 6, more especially 1 to 4 carbon atoms. Preferred alkyl groups are methyl and ethyl.

Especially preferred compounds according to the present invention are those of formula 1 in which $R_1$, $R_2$, $R_3$ and $R_4$ independently represent hydrogen or $C_1$–$C_4$ alkyl, especially methyl, provided that at least one of them represents alkyl, or $R_1$ together with $R_3$ represents a second valency bond joining their immediately adjacent carbon atoms and $R_2$ and $R_4$ are as defined above provided that at least one of them represents alkyl;

Y represents $C_1$–$C_4$ alkoxy, especially methoxy, halogen, especially chlorine, or trifluoromethyl;

m represents zero or 1;

A represents $C_1$–$C_6$ alkylene, especially of the formula $-(CH_2)_n-$ wherein n represents 2, 3 or 4;

$R_5$ represents $C_1$–$C_4$ alkyl, especially methyl or ethyl;

$R_6$ represents hydrogen or, preferably $C_1$–$C_4$ alkyl especially methyl or ethyl;

$R_7$ and $R_8$, if present, independently represent $C_1$–$C_4$ alkyl, especially methyl or ethyl or together with the amino nitrogen atom represent a saturated six-membered heterocyclic ring optionally substituted by oxygen or further nitrogen atoms, e.g. piperidino, piperazino or especially morpholino; and D, if present, represents oxygen, and acid addition salts thereof.

Particularly preferred esters of the present invention include those of formula 2a:

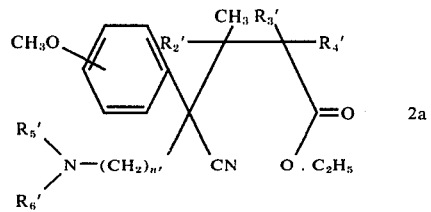

wherein $n'$ represents 2 or 3;

$R_2'$, $R_3'$ and $R_4'$ independently represent hydrogen or methyl, and $R_5'$ and $R_6'$ independently represent methyl or ethyl, and acid addition salts thereof.

Particularly preferred amides of the present invention include those of formula 2b:

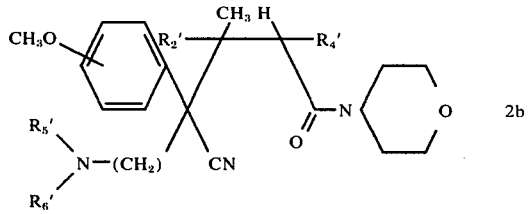

wherein $n'$ represents 2 or 3;

$R_2'$ and $R_4'$ independently represent hydrogen or methyl; and $R_5'$ and $R_6'$ independently represent methyl or ethyl.

The compounds of the present invention which have been pharmacologically screened to date have a useful level of central nervous system, in particular antidepressant, activity as measured by standard screening tests, with little or no parasympatholytic activity.

Further, the compounds are believed to have a therapeutically useful level of cardiovascular activity. They are believed to be vasodilators and/or cardiostimulators and/or to affect cardiac output. They are useful also as intermediates in the preparation of the novel pharmacologically active pyridine derivatives of our co-pending Application No. 59761/72, the disclosure of which application is incorporated herein by reference.

The mydriatic activity of each of the compounds was assessed by subcutaneously administering various doses of each compound in a suitable vehicle to groups of 5 mice and after 30 minutes measuring their pupillary diameters in arbitrary units using a binocular microscope. The mean diameters of each group were then plotted on a dose/response curve taking the mean diameter of a 5 mice group treated with the vehicle as O and of a similar group treated with 1 mg/kg atropine in the vehicle as 100% mydriasis. The dose of compound required to induce 50% mydriasis was calculated from the dose/response curve. It is generally accepted that the degree of mydriasis is an indication of the extent of parasympatholytic activity; the lower the $MYD_{50}$, the greater the parasympatholytic activity. All the compounds tested had a $MYD_{50}$ well in excess of 256.

The interaction with amphetamine of each of the compounds was determined using a modification of the method described by Quinton R. M. and Halliwell G. in Nature (Lond.) 1963, 200: 178–9. Various doses of each compound in a suitable vehicle were administered intraperitoneally to groups of 4 rats one hour before similarly administering 5 mg/kg of d-amphetamine. The degree of stereotypy of each rat was assessed every 30 minutes following administration of amphetamine for a period of 6 hours using the 6 point scale of Quinton and Halliwell (supra). The mean peak score for each group was compared with that of a control group of 4 rats who received vehicle and amphetamine in the sequence reported above. The control group ususally scored 50% of the maximum possible score so the test compound was considered to induce moderate potentiation (+) if the peak score was 60–75% of maximum and marked potentiation (++) if the peak score was 75–100%.

The behaviour of the control group returned to normal before 5 hours post amphetamine. Therefore to indicate the degree of prolongation of amphetamine stereotypy the mean score of each group at 5–6 hours was compared with the peak score. For control groups the value of $$\frac{\text{5-6 hour score}}{\text{Peak score}} \times 100$$

was always less than 30, so a compound was considered to induce slight prolongation (+) if the value was between 30 and 55, moderate prolongation (++) if the value was between 55 and 80 and marked prolongation (+++) if the value was between 80 and 100. A typical result for the compounds tested was slight potentiation and marked prolongation at a dose between 5 and 50 sc.

The esters of the invention in which at least one of $R_3$ or $R_4$ represents hydrogen can be prepared from the corresponding 4-aminoalkyl-4-cyano-4-phenyl-1-alkoxy or alkylthio-1-dialkylamino or saturated heterocyclic amino-but-1-ene or but-1,2-diene. In terms of preparing compounds of formula 1, the said butene or butadiene starting material will be of the formula 3:

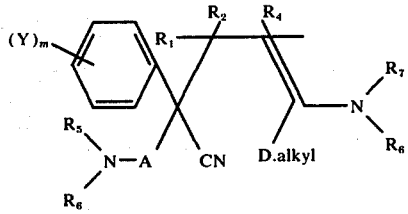

wherein the symbols are as defined in connection with formula 1.

The process for converting the butene or butadiene starting materials into the desired nitrile ester comprises a first step in which the corresponding 4-aminoalkyl-4-phenyl-3 and/or 2 alkyl or alkylene-1-dialkoxy-1-alkoxy or alkylthio-butane or but-2-ene is formed by treating the starting material with, for example, a strong non-nucleophilic acid, such as methane sulphonic acid, in the presence of a mixture of a $C_1$–$C_6$ primary alcohol, such as ethanol, and orthoester, such as ethyl orthoformate. The reaction usually will be carried out at an elevated temperature, advantageously in the range 60° to 120° C and preferably under reflux conditions.

The butane or butene intermediate prepared as above is then hydrolysed, usually in situ, by treatment with, for example, water at an elevated temperature, especially 60° to 90° C, to the desired ester.

In a typical process for preparing compounds of the invention from the aforementioned butene and butadiene starting materials, the starting material (1 equivalent) is dissolved in ethanol and ethyl orthoformate (5 equivalents) and methane sulphonic acid (3 equivalents) added to the resultant solution. Said solution is refluxed overnight and then poured into water. The aqueous mixture is maintained at 70° C for 30 minutes and then cooled, washed with ether, adjusted to pH7 and added to a suspension of p-toluene sulphonyl chloride in 5N sodium hydroxide. The mixture is shaken vigorously for 15 minutes with cooling, if necessary. The product is extracted into ether, the ethereal solution washed with dilute hydrochloric acid and the aqueous solution added to saturated potassium carbonate solution. The basic organic materials are then extracted into ether and recovered by drying over magnesium sulphate and evaporating off the solvent. The ester product thus obtained may be contaminated with some corresponding amide which can be separated by column chromatography.

The alkyl esters of 4-aminoalkyl-4-cyano-4-phenyl-3- and/or 2-alkyl or alkylene-but-2-enoic acids of the invention may also be prepared by treating an alkali metal, preferably sodium, α-aminoalkyl-benzyl-cyanide with an alkyl ester of 3 and/or 2-alkyl or alkylene-prop-1-enoic acid having a leaving group in the 3-position. By a leaving group we mean a group which under the reaction conditions employed will preferentially form an alkali metal salt. Suitable leaving groups include p-toluene sulphonyl or benzene-sulphonyl. Usually, the reaction will be carried out in a polar aprotic solvent such as dimethylsulphoxide and preferably at a temperature in the range 50° to 100° C.

In terms of preparing the compounds of formula 1 wherein $R_1$ and $R_3$ together represent a second valency bond between the adjacent carbon atoms, the said propenoic acid alkyl esters are of the formula 4:

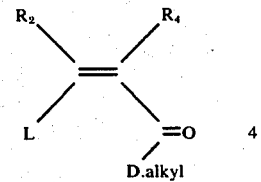

wherein L represents the leaving group and the other symbols are as defined in connection with formula 1. When $R_2$ is alkyl with an α-hydrogen atom, the reaction product is an isomer of the said compound of formula 1 in which the 2, 3 bond is unsaturated and an ethylene double bond extends from the 3-position to the residue of the group $R_2$ after removal of the α-hydrogen atom i.e. of the formula 1a:

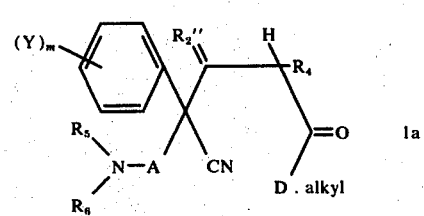

wherein $R''_2$ represents the residue of an alkyl group of 1 to 4 carbon atoms having an α-hydrogen atom after removal of that atom, and the remaining symbols are as defined in connection with formula 1.

The alkyl esters of 4-aminoalkyl-4-cyano-4-phenyl-3-alkyl or alkylene-2-alkoxycarbonyl-butanoic acids may be prepared by treating an alkali metal, preferably sodium, α-aminoalkylbenzyl cyanide with a dialkyl ester of 2-alkyl or alkylene-ethylene-1,1-dicarboxylic acid. In terms of preparing compounds of formula 1, the said diesters are of the formula 5:

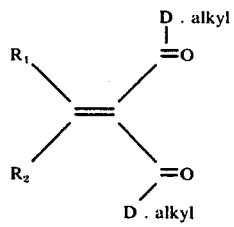

wherein the symbols are as defined in connection with formulae 1 and 2. It is doubtful, however, if the process would proceed as desired when both $R_1$ and $R_2$ represent alkyl groups having α-hydrogen atoms.

Usually the aforementioned reaction will take place by heating the reactants in an anhydrouspolar solvent such as dimethyl sulphoxide or dioxan to a temperature in the range of 40° to 100° C, preferably at 50° to 70° C, for a period of up to about 3 hours. The reaction mixture is then cooled and neutralised with a weak anhydrous acid such as acetic acid. After removal of the solvent, the residue may be dissolved in water, added to a saturated potassium carbonate solution and the desired nitrile ester extracted into ether.

The amides of the invention can be obtained by treating the 4-aminoalkyl-4-cyano-4-phenyl-3 and/or 2 alkyl or alkylene-1-alkoxy or alkylthio-1-dialkylamino or saturated heterocyclic amino-but-1-ene or but-1,2-diene with sodium iodide and a strong acid, e.g. methane sulphonic acid, in a solvent, e.g. ethanol. It is preferred to heat the reaction mixture. Any iodine produced during the reaction can be destroyed by treatment with, for example, sodium bisulphite solution.

The processes described above can be employed to prepare all of the compounds of the present invention although in some cases direct formation of a particular compound may not be possible. However, it will be readily apparent to those skilled in the art that those compounds which cannot be prepared directly by the said processes can be obtained by methods known per se from related compounds of the invention which can be prepared directly. In other cases, it may be desirable for a substituent in a compound prepared according to one of the aforementioned processes to be converted into another substituent to provide another compound of the invention. These conversions are carried out in manner known per se. Thus, for example, a compound of formula 1 in which $R_4$ represents alkoxycarbonyl can readily be converted into the corresponding compound in which $R_4$ represents hydrogen by heating with a mineral acid, for example hydrochloric acid in acetic acid solution.

The compounds produced by the foregoing process may be isolated per se. However, since they are generally liquids they may be more conveniently isolated as their acid addition salts.

The acid addition salts are preferably the pharmaceutically acceptable, non-toxic addition salts with suitable acids, such as those with inorganic acids, for example hydrochloric, hydrobromic, sulphuric or phosphoric acids, or with organic acids, such as organic carboxylic acids, for example, glycollic, maleic, hydroxymaleic, malic, tartaric, citric, salicylic, o-acetyloxybenzoic, nictinic or isonicotinic acid, or organic sulphonic acids for example methane sulphonic, ethane sulphonic, 2-hydroxyethane sulphonic, toluene-sulphonic or napthalene-2-sulphonic acid. Apart from pharmaceutically acceptable acid addition salts, other salts are also included within the scope of acid addition salts such as, for example, those with picric or oxalic acid; they may serve as intermediates in the purification of the compounds or in the preparation of other, for example, pharmaceutically acceptable, acid addition salts, or are useful for identification, or characterisation of the bases.

A resulting acid addition salt may be converted into the free compound according to known methods, for example, by treating it with a base, such as with a metal hydroxide or alkoxide, for example an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate; with ammonia; or with a hydroxyl ion exchange preparation, or with any other suitable reagent.

A resulting acid addition salt may also be converted into another acid addition salt according to known methods, for example, a salt with an inorganic acid may be treated with a metal salt, for example a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

In the composition aspect of the invention, there are provided pharmaceutical formulations in which form the active compounds of the invention will normally be utilised usually in the form of a pharmaceutically acceptable acid addition salt. Such formulations are prepared in a manner known per se in the pharmaceutical art and usually comprise at least one active compound of the invention in admixture or otherwise in association with a pharmaceutically acceptable carrier therefore. For making these formulations, the active ingredient will usually be mixed with a carrier, or diluted by a carrier, or enclosed or encapsulated in a capsule, sachet, cachet, paper or other container. A carrier or diluent may be a solid, semi-solid or liquid material which serves as a vehicle, excipient, or medium for the active ingredient. Some examples of such diluents or carriers are lactose, dextrose, sucrose, sorbitol, mannitol, starches, gum acacia, calcium phosphate, liquid paraffin, cocoa butter, oil of theobroma, alginates, tragacanth, gelatin, syrup B.P., methyl cellulose, polyoxyethylene benzoate, talc, magnesium stearate or mineral oil.

The formulations of the invention may be adapted for enteral or parenteral use and may be administered to a subject requiring treatment in the form of tablets, capsules, suppositories, solutions, suspensions or the like. The dosage required for the treatment of any animal will depend upon the route of administration and will usually fall within the range 0.01 to 250 mg/kg, more especially 0.04 to 40 mg/kg, daily. In the case of humans much further work remains to be done before a safe and effective dosage can be recommended but it is expected that said dosage will be within the range 0.05 to 100 mg/kg daily. Accordingly, formulations of the invention are likely to be provided in dosage unit forms containing from 1 to 1000 mg, more likely 1 to 100 mg and most likely 1 to 50 mg.

The following Examples will further illustrate the preparation of the novel compounds of this invention. All temperatures are given in degrees Centigrade.

EXAMPLE 1

Preparation of ethyl-4-cyano-4-(m-methoxyphenyl)-4-($\beta$-N,N-dimethylaminoethyl)-3-ethyl-2-ethoxycarbonylbut-2-enoate Sodium hydride (2.83 g of a 50% suspension in oil) is dissolved in dry dimethylsulphoxide and $\alpha$-(2-N,N-dimethylaminoethyl)-m-methoxy benzyl cyanide (12.9 g) added. Diethyl-1-(benzenesulphonyloxy)-propylidine malonate (21 g) is added slowly to the resultant mixture. The solvent is then removed and the residue "topped" at 0.1 mm Hg and 150° to leave crude ethyl-4-cyano-4-($\beta$-N,N-dimethylaminoethyl)-4-(m-methoxyphenyl)-3-ethyl-2-ethoxycarbonyl-but-2-enoate.

This crude ester is dissolved in ethanol and then an ethanolic solution of an equivalent quantity of oxalic acid dihydrate added. The resultant solution is evaporated to dryness and the residue recrystallised from isopropanol to yield the hydrogen oxalate salt of the ester in the pure state.

A solution of said crude ester (6.3 g) in acetic acid (10 ml) and sulphuric acid (12 ml) was held at 100° for 1 hour and then cooled. The cooled mixture was poured onto ammonia/ice, the pH adjusted to 8 by addition of aqueous ammonia and the precipitated gum triturated with methanol. The solid was filtered off and recrystallised from aqueous methanol to give white crystals of 3(m-methoxyphenyl)-3-($\beta$-N,N-dimethylaminoethyl)-4-ethyl-5-ethoxycarbonyl-2,6-dioxotetrahydropyridine, m.p. 160°–2°.

EXAMPLE 2

Preparation of ethyl-4-cyano-4-(m-methoxyphenyl)-4-($\gamma$-N,N-dimethylaminopropyl)-3,3-dimethyl-butanoate $\alpha$(3-N,N-Dimethylaminopropyl)-m-methoxy benzyl cyanide (16.9 g, 0.07 mole) was added to a stirred solution of dimsyl sodium (prepared from sodium hydride (3.6 g, 50%; 0.07 mole) and 60 ml dimethylsulphoxide) cooled in a water bath and in a nitrogen atmosphere. To the stirred solution was added dropwise a solution of 3,3-dimethyl-1-ethoxy-prop-2-enylidene morpholinium tetrafluoroborate (20.7 g; 0.07 mole) in dimethylsulphoxide and the mixture finally heated at 50°–60° for 2 hours. The dimethyl sulphoxide was evaporated off at 0.1 mm, the residue washed several times with dry ether and the ether solutions evaporated to give a red oil (basic ketene acetal)(26.2 g). This oil was dissolved in dioxan (150 ml), water(9 ml) added and the mixture allowed to stand overnight at room temperature. The mixture was poured into water (500 ml) containing potassium carbonate solution (30 ml) and the separated oil isolated by ether extraction. An infrared spectrum of the oil indicated that it was a mixture of ethyl 4-($\gamma$-N,N-dimethylaminopropyl)-4-cyano-4-(m-methoxyphenyl)-3,3-dimethyl butanoate, the corresponding morpholide and the basic cyanide starting material. The material was subjected to column chromatography using an alumina column and Pet-ether (40–60) as the eluate. Evaporation of the fractions gave various mixtures of starting material and the required ester, the morpholide remaining on the column. Separation of the mixture by fractional crystallisation of the oxalate salts failed and therefore the mixture was hydrolysed using refluxing alcoholic potassium hydroxide (approximately one equivalent). The alcohol was evaporated off, the residue dissolved in water, and the oily starting material removed by ether extraction. The pH of the aqueous solution was adjusted to 8, the amino acid extracted into chloroform, and the dried chloroform solution evaporated.

The residue was converted to its hydrochloride by the addition of normal hydrochloric acid and evaporation of the slight excess at 0.1mm. Refluxing the hydrochloride with absolute ethanol for 3 hours, evaporation of the ethanol and recrystallisation of the residue from methyl ethyl ketone gave ethyl 4-($\gamma$-N,N-dimethylaminopropyl)-4-cyano-4-(m-methoxyphenyl)-3,3-dimethyl benzoate hydrochloride mp 166°–8° (2.1 g).

Found C 62.97 H, 8.17, N 6.8 Cl 8.92; Calculated C 63.51 H 8.38, N 7.06, Cl 8.94.

The ester prepared as above (28.8 g) is dissolved in 2.5 N hydrochloric acid (100 ml) and the solution refluxed for 3½ hours and then allowed to cool. The crystals thus formed (21.0 g) are washed with 5N hydrochloric acid and dried. These crystals soften at 270° C and melt at 290° C and their analysis corresponds to $C_{19}H_{29}C\ N_2O$. The crystals are dissolved in water and the resultant solution neutralised with ammonium hydroxide and then extracted with chloroform (three times). The chloroform solutions are combined, the solvent removed by heating and the residue recrystallised from aqueous methanol to yield 3-(m-methoxyphenyl)-3-($\gamma$-N,N-dimethylaminopropyl)-4,4-dimethyl-2,6-dioxo-piperidine m.pt. 168°–170°.

EXAMPLE 3

4-($\gamma$-N-benzyl-N-methyl-aminoethyl)-4-cyano-4 (m-methoxyphenyl)-2-methyl-butanoic acid morpholine amide.

Sodium Hydride (16.8 g) was dissolved in dimethylsulphoxide under nitrogen and $\alpha$(2-N-Benzyl-N-methylaminoethyl)-m-methoxyphenyl benzyl cyanide (102.9 gm) added. To the stirred solution was added a solution in dimethylsulphoxide of O-ethyl methacryoylmorpholinium tetrafluoroborate (from 54.25 gm methacryloyl morpholine and 66.5 gm Et$_3$OBF$_4$). When addition was complete, the mixture was held at 70° C for 1 hour.

After cooling, a 50 ml aliquot was withdrawn, diluted with 100 ml water and extracted with ether (3 × 50 ml). The ethereal solutions were combined, dried etc. The residue contained ester, amide and acetal. Hydrolysis of the mixture in moist dioxan at 100° for 30 mins. gave 65% ester 35% amide.

Since the ester was required for the synthesis actually being attempted, the bulk of the original dimethylsulphoxide solution was evaporated to dryness and extracted with dry Et$_2$O. After hydrolysis a mixture containing 80% ester was obtained and combined with the earlier mixture. An attempt to separate via oxalates failed, so the mixture was dissolved in absolute ethanol, KOH was added and the mixture stirred at room temperature overnight. The ethanol was removed under vacuum on a cold water bath, the residue dissolved in water and extracted with ether. The ether extracts yielded a mixture of amide and unreacted starting material. The amide containing mixture was adsorbed onto basic alumina and chromatographed (45 × 2 cm) starting with 40–60 petrol. Early fractions (of 250 ml each) contained only unreacted starting material. The polarity was increased too early and amide started coming through at fraction 5. N.m.r. of fraction 7 showed two methyl doublets. Crystals which grew in fraction 5 were found to have the lower field methyl absorption. The column was stripped with chloroform and all amide containing fractions combined and re chromatographed with 40–60 petrol.

The first two (250 ml) fractions contained starting material. The next ten, upon standing overnight, were seen to contain crystals. These were combined and recrystallised from Ethyl acetate + 40–60 petrol mp 102°–3°.

n.m.r. showed them to be "low field" isomer. Analysis $C_{27}H_{35}N_3O_3 = 449$.

|  | C | H | N |
|---|---|---|---|
| Requires | 72.16 | 7.80 | 9.35 |
| Found | 72.22 | 7.82 | 9.46 |

EXAMPLE 4

4-(γ-N,N-dimethylaminopropyl)-4-cyano-4-(m-methoxyphenyl)-3,3-dimethyl-butanoic acid morpholine amide The free morpholide was prepared as described in Example 3. It was extracted off the alumina column using ether.

A solution of the syrupy morpholide in acetone was treated with an equivalent of oxalic acid dihydrate in acetone, and the solid which crystallised out recrystallised from acetonitrile to give 4-(γ-N,N-dimethylaminopropyl)-4-cyano-4-methoxyphenyl-3,3-dimethyl butanoic acid morpholine amide hydrogen oxalate.

mp 171°–3° Found C, 60.87, H 7.51, N 8.84; $C_{25}H_{37}N_3O_7$ C, 61.08 H 7.59 H, 8.55.

EXAMPLE 5

4-(β-N,N-dimethylaminoethyl)-4-cyano-4-(m-methoxyphenyl)-2,3-dimethyl-butanoic acid morpholine amide.

4-(β-N,N-dimethylaminoethyl)-4-cyano-4-(m-methoxyphenyl)-3,2-dimethyl-1-ethoxy-1-morpholinobut-1-ene was dissolved in alcohol, a solution of methane sulphonic acid (2 equivalents) in alcohol added followed by an alcoholic solution of sodium iodide. The mixture was heated for 1 hour in a warm water bath. Traces of iodine formed were destroyed with sodium bisulphite solution. The solution was then evaporated down under reduced pressure until only a small volume of solvent remained. Water was then added and the mixture extracted with ether. The aqueous solution was poured into excess saturated potassium carbonate solution and the basic cyano amide extracted into ether. After drying etc. the ether was removed leaving a sticky residue. The oxalate was prepared by treating with alcoholic oxalic acid and removing the solvent. This also left a gummy residue which was triturated with hot ethyl acetate. The solvent was decanted off, left to stand, yielding a white precipitate. Crystallisation from propionitrile gave a material which was analytically pure II oxalate, m.p. 173.–5. The base was recovered from this and cyclised in 20% by weight $H_2SO_4$ in HOAc. This yielded 'lowfield' isomer after crystallisation from Aq. MeOH.

EXAMPLE 6

The following compounds of the invention are also prepared by methods disclosed in this Specification:

4-(β-N,N-dimethylaminoethyl)-4-cyano-4-phenyl-3-methylbutanoic acid ethyl ester;

4-(β-N,N-dimethylaminoethyl)-4-cyano-4-phenyl-2-methylbutanoic acid ethyl ester;

4-(β-N,N-dimethylaminoethyl)-4-cyano-4-(m-methoxyphenyl)-2-methyl-butanoic acid ethyl ester;

4-(β-N,N-dimethylaminoethyl)-4-cyano-4-(m-methoxyphenyl)-3-methyl-butanoic acid ethyl ester;

4-(β-N,N-dimethylaminoethyl)-4-cyano-4-phenyl-3,3-dimethylbutanoic acid ethyl ester;

4-(β-N,N-dimethylaminoethyl)-4-cyano-4-(m-methoxyphenyl)-3,3-dimethyl-butanoic acid ethyl ester;

4-(β-N,N-dimethylaminoethyl)-4-cyano-4-(m-methoxyphenyl)-2,3-dimethyl-butanoic acid morpholine amide;

4-(β-N,N-dimethylaminoethyl)-4-cyano-4-(m-methoxyphenyl)-2,3-dimethyl-butanoic acid morpholine amide oxalate.

4-(β-N,N-dimethylaminoethyl)-4-cyano-4-phenyl-2,3-dimethyl-butanoic acid morpholine amide.

4-(γ-N,N-dimethylaminopropyl)-4-cyano-4-phenyl-3,3-dimethyl-butanoic acid ethyl ester;

4-(γ-N,N-dimethylaminopropyl)-4-cyano-4-(p-chlorophenyl)-3,3-dimethyl-butanoic acid ethyl ester;

4-(γ-N,N-dimethylaminopropyl)-4-cyano-4-(m-methoxyphenyl)-3,3-dimethyl-butanoic acid ethyl ester;

4-(β-N-benzyl-N-methylaminoethyl)-4-cyano-4-phenyl-3,3-dimethyl-butanoic acid ethyl ester;

4-(β-N-benzyl-N-methylaminoethyl)-4-cyano-4-(m-methoxyphenyl)-3,3-dimethyl-butanoic acid ethyl ester;

4-(γ-N,N-dimethylaminopropyl)-4-cyano-4-(m-methoxyphenyl)-2,3-dimethyl-butanoic acid ethyl ester;

4-(β-N-methyl-N-(m,p dimethoxyphenethyl)-aminoethyl)-4-cyano-4-(m,p dimethoxyphenyl)-3,3-dimethyl-butanoic acid ethyl ester hydrogen maleate; and 4-(β-N-methyl-N-(m,p-dimethoxyphenethyl)-aminoethyl)-4-cyano-4-(3′, 5′-dimethoxyphenyl)-3,3-dimethyl-butanoic acid ethyl ester.

In the following examples of pharmaceutical compositions, the term "medicament" is used to indicate the compound ethyl-4-cyano-4-(m-methoxyphenyl)-4-(γ-N,N-dimethyl aminopropyl) 3,3-dimethyl-butanoate. That compound may of course be replaced in these compositions by another compound of the invention and the amount of medicament may be increased or decreased as is well known in the art depending on the degree of activity of the medicament used.

EXAMPLE 7

| Tablet formulation | mg/tablet |
|---|---|
| Medicament | 15 |
| Lactose | 86 |
| Maize Starch (dried) | 45.5 |
| Gelatin | 2.5 |
| Magnesium stearate | 1.0 |

The medicament is powdered and passed through a B.S. No. 100 sieve and well mixed with the lactose and 30 mg of the maize starch, both passed through a B.S. No. 44 sieve.

The mixed powders are massed with a warm gelatin solution prepared by stirring the gelatin in water and heating to form a 10 w/w solution. The mass is granulated by passing through a B.S. No. 12 sieve and the moist granules dried at 40° C.

The dried granules are re-granulated by passing through a B.S. No. 14 sieve and the balance of the starch sieved 44 mesh and the magnesium stearate sieved 60 mesh are added and thoroughly mixed.

The granules are compressed to produce tablets each weighing 150 mg.

EXAMPLE 8

| Tablet formulation | mg/Tablet |
|---|---|
| Medicament | 100 |
| Lactose | 39 |
| Maize starch (dried) | 80 |
| Gelatin | 4.0 |
| Magnesium stearate | 2.0 |

The method of preparation is identical with that of Example 7 except that 60 mg of starch is used in the granulation process and 20 mg during tabletting.

EXAMPLE 9

| Capsule formulation | mg/capsule |
|---|---|
| Medicament | 250 |
| Lactose | 150 |

The medicament and lactose are passed through a No. 44 B.S. sieve and the powders well mixed together before filling into hard gelatin capsules of suitable size, so that each capsule contained 400 mg of mixed powders.

EXAMPLE 10

| Suppositories | mg/suppository |
|---|---|
| Medicament | 50 |
| Oil of Theobroma | 950 |

The medicament is powdered and passed through a B.S. No. 100 sieve and triturated with molten oil of Theobroma at 45° C to form a smooth suspension.

The mixture is well stirred and poured into moulds, each of nominal 1 G capacity, to produce suppositories.

EXAMPLE 11

| Cachets | mg/cachet |
|---|---|
| Medicament | 100 |
| Lactose | 400 |

The medicament is passed through a B.S. No. 40 mesh sieve, mixed with lactose previously sieved 44 mesh and filled into cachets of suitable size so that each contained 500 mg.

EXAMPLE 12

| Intramuscular Injection (Suspension in aqueous vehicle) | |
|---|---|
| Medicament | 10 mg |
| Sodium Citrate | 5.7 mg |
| Sodium carboxymethylcellulose (low viscosity grade) | 2.0 mg |
| Methyl para-hydroxybenzoate | 1.5 mg |
| Propyl para-hydroxybenzoate | 0.2 mg |
| Water for Injection | to 1.0 ml |

The sodium citrate and sodium carboxymethylcellulose are mixed with sufficient water for injection at 80° C.

The mixture is cooled to 50° C and the methyl and propyl para-hydroxybenzoates added followed by the medicament previously milled and sieved 300 mesh. When cool the injection is made up to volume and sterilised by heating in an autoclave.

We claim:

1. Alkyl esters and salts of the formula

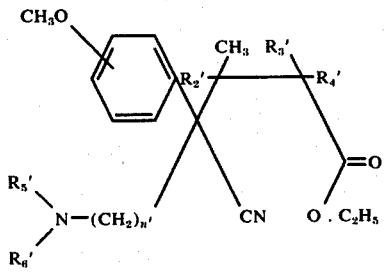

wherein
n' represents 2 or 3;
$R_2'$, $R_3'$, and $R_4'$, independently represent hydrogen or methyl, and
$R_5'$, and $R_6'$ independently represent methyl or ethyl.

2. Alkyl esters and salts selected from:
4-($\beta$-N,N-dimethylaminoethyl)-4-cyano-4-phenyl-3-methyl-butanoic acid ethyl ester and acid addition salts thereof;
4-($\beta$-N,N-dimethylaminoethyl)-4-cyano-4-phenyl-2-methyl-butanoic acid ethyl ester and acid addition salts thereof;
4-($\beta$-N,N-dimethylaminoethyl)-4-cyano-4-(m-methoxyphenyl)-2-methyl-butanoic acid ethyl ester and acid addition salts thereof;
4-($\beta$-N,N-dimethylaminoethyl)-3-cyano-4-(m-methoxyphenyl)-3-methyl-butanoic acid ethyl ester and acid addition salts thereof;
4-($\beta$-N,N-dimethylaminoethyl)-4-cyano-4-phenyl-3,3-dimethyl-butanoic acid ethyl ester and acid addition salts thereof;

4-(β-N,N-dimethylaminoethyl)-4-cyano-4-(m-methoxyphenyl)-3,3-dimethyl-butanoic acid ethyl ester and acid addition salts thereof;

4-(γ-N,N-dimethylaminopropyl)-4-cyano-4-phenyl-3,3-dimethyl-butanoic acid ethyl ester and acid addition salts thereof;

4-(γ-N,N-dimethylaminopropyl)-4-cyano-4-(p-chlorophenyl)-3,3-dimethyl-butanoic acid ethyl ester and acid addition salts thereof;

4-(γ-N,N-dimethylaminopropyl)-4-cyano-4-(m-methoxyphenyl)-3,3-dimethyl-butanoic acid ethyl ester and acid addition salts thereof;

4-(β-N-benzyl-N-methylaminoethyl)-4-cyano-4-phenyl-3,3-dimethyl-butanoic acid ethyl ester and acid addition salts thereof;

4-(β-N-benzyl-N-methylaminoethyl)-4-cyano-4-(m-methoxyphenyl)-3,3-dimethyl-butanoic acid ethyl ester and acid addition salts thereof;

4-(γ-N,N-dimethylaminopropyl)-4-cyano-4-(m-methoxyphenyl)-2,3-dimethyl-butanoic acid ethyl ester and acid addition salts thereof;

4-(β-N-methyl-N-(m,p dimethoxyphenethyl)-aminoethyl-)-4-cyano-4-(m,p dimethoxyphenyl)-3,3-dimethylbutanoic acid ethyl ester and acid addition salts thereof, and 4-(β-N-methyl-N-(m,p dimethoxyphenethyl)-aminoethyl-4-cyano-4-(3′, 5′-dimethoxyphenyl)-3,3-dimethyl-butanoic acid ethyl ester and acid addition salts thereof.

3. A compound in accordance with claim 1, which is ethyl-4-cyano-4-(m-methoxyphenyl)-4-(γ-N,N-dimethylaminopropyl)-3,3-dimethyl-butanoate.

4. A pharmaceutical composition in a dosae unit form containing 1 to 1000 mg of a compound of claim 1 per dosage unit, and a pharmaceutically acceptable carrier.

* * * * *